United States Patent [19]
Howard, III

[11] Patent Number: 5,925,050
[45] Date of Patent: Jul. 20, 1999

[54] SELF-CLEARING BONE BITING INSTRUMENT

[75] Inventor: Matthew A. Howard, III, Iowa City, Iowa

[73] Assignee: The University of Iowa Research Foundation, Iowa City, Iowa

[21] Appl. No.: 08/912,182

[22] Filed: Aug. 15, 1997

[51] Int. Cl.⁶ .................................................. A61B 17/00
[52] U.S. Cl. .......................... 606/83; 606/170; 606/184
[58] Field of Search ........................... 606/83, 170, 184; 600/567, 562

[56] References Cited

U.S. PATENT DOCUMENTS

| | | | |
|---|---|---|---|
| 3,902,498 | 9/1975 | Niederer | 128/305 |
| 4,201,213 | 5/1980 | Townsend | 128/312 |
| 4,722,338 | 2/1988 | Wright et al. | 128/312 |
| 4,777,948 | 10/1988 | Wright | 128/312 |
| 5,273,519 | 12/1993 | Koros et al. | 606/83 |
| 5,385,570 | 1/1995 | Chin et al. | 606/170 |
| 5,451,227 | 9/1995 | Michaelson | 606/83 |
| 5,569,258 | 10/1996 | Gambale | 606/83 |
| 5,582,618 | 12/1996 | Chin et al. | 606/170 |
| 5,766,177 | 6/1998 | Lucas-Dean et al. | 606/83 |

Primary Examiner—Michael Buiz
Assistant Examiner—Julian W. Woo
Attorney, Agent, or Firm—Fleshner & Kim

[57] ABSTRACT

A self-clearing bone biting surgical instrument comprises a stationary lower arm, including a lower arm recess and a foot plate; and a reciprocating upper arm, including a cutting tip located at its distal end for engagement with the foot plate in order to effect cutting or punching of tissue positioned between the foot plate and the cutting tip. An ejecting unit movable within the lower arm recess forcibly ejects debris lodged against the foot plate as the upper arm reciprocates rearwardly as part of the normal operating process of the instrument. A method of making a self-clearing bone biting instrument of the invention is also disclosed.

56 Claims, 15 Drawing Sheets

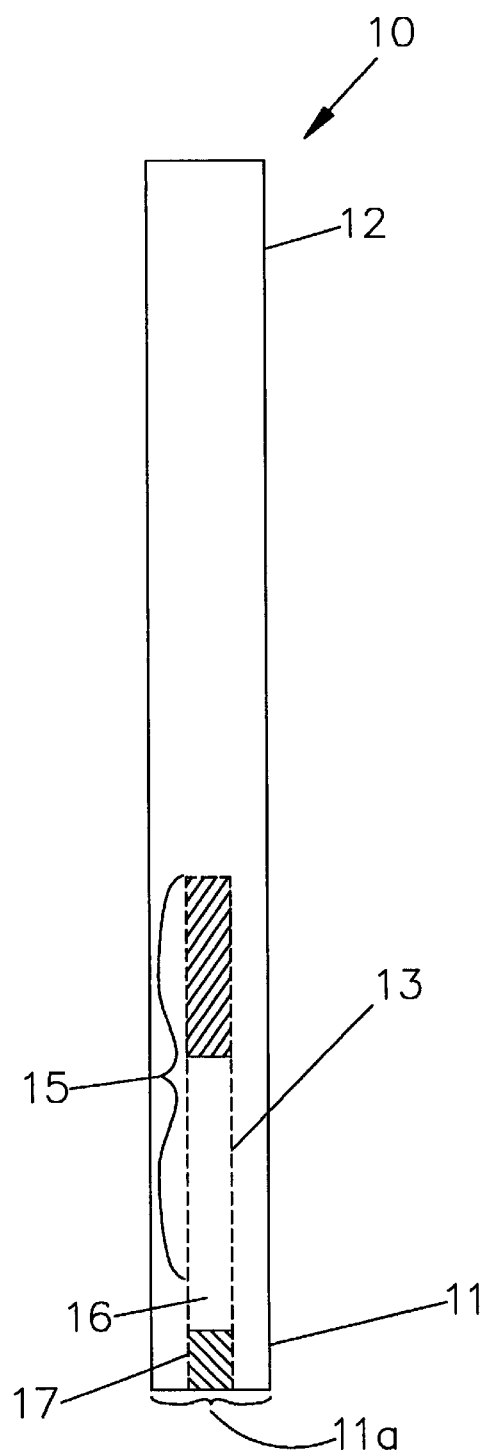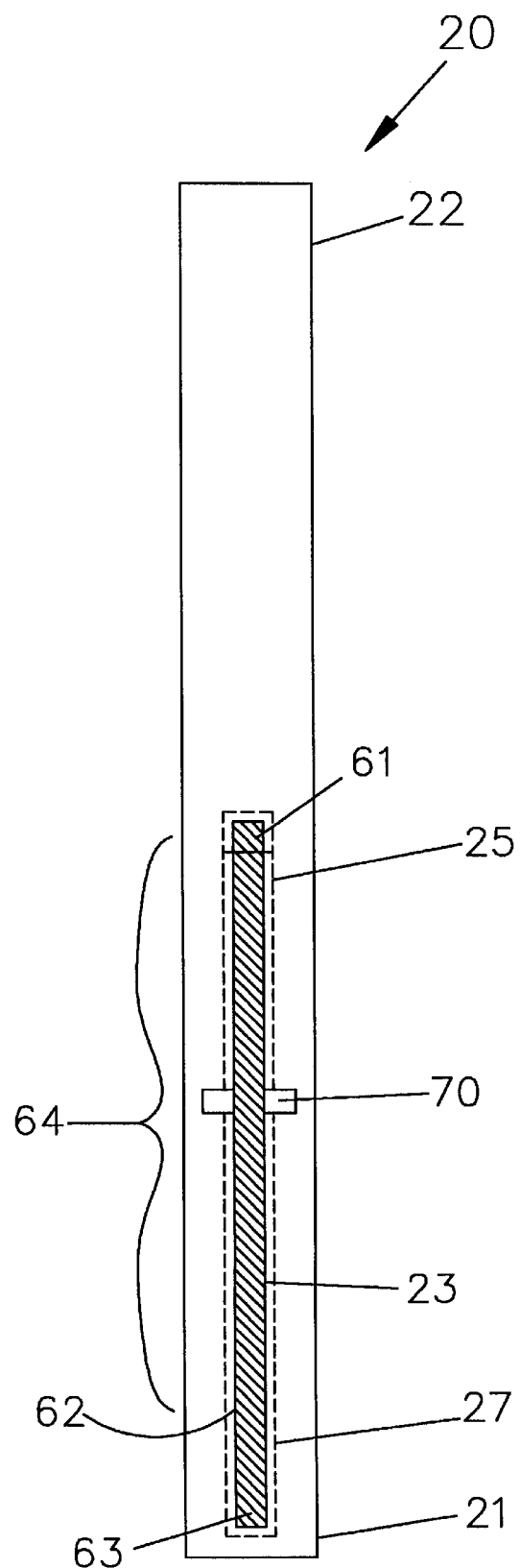
FIG. 4B
FIG. 4A

SELF-CLEARING BONE BITING INSTRUMENT

BACKGROUND OF THE INVENTION

1. Field of the Invention

This invention relates to a surgical instrument for cutting hard tissues such as bone and cartilage. In particular, this invention relates to a bone cutting or bone biting instrument or rongeur in which the jaws of the instrument are self-cleared after each bite of the instrument. More particularly, this invention relates to a self-clearing bone-biting instrument in which an ejecting unit serves to dislodge bone fragments from the jaws of the instrument. This invention further relates to a method of making a self-clearing bone biting instrument.

2. Background of the Related Art

Bone-biting instruments or rongeurs are common surgical instruments designed to cut, nibble, or grip bone or other tissues. Thus rongeurs are commonly used in spinal surgery to cut away bone overlying the spinal cord; and in neurosurgery to cut away the cervical area of the spine, or the skull.

A number of different types of rongeurs are available, as will be described hereinbelow. Typically, bone-biting surgical instruments include a lower stationary cutting element or arm, including a foot plate element or anvil at its distal end and a handle at its proximal end. An upper movable cutting element or arm includes a distal end which acts as an upper jaw for use in cooperation with the foot plate element. An actuator causes the distal end of the movable upper arm to be forced against the foot plate element, thereby cutting, biting, or punching out fragments of bone positioned against the foot plate.

Usually many bites must be taken with such an instrument during a single surgical procedure. For example, during a conventional spine operation the surgeon may make 10 to 20 bites with a bone-biting instrument. After each bite, the jaws of the instrument are cleared, e.g. by the surgeon or surgical assistant swiping the jaws of the instrument against a towel or sponge, to remove any fragments of cut bone or other debris that may have become lodged therein. Removal of bone fragments between each bite forces interruption of the surgical procedure and causes the surgeon to repeatedly refocus his or her attention to the task in hand, and results in unnecessary delay. Furthermore, occasionally a fragment of bone becomes very solidly lodged in the jaws of the instrument such that the fragment can only be removed by exerting considerable pressure from a pointed instrument. In which case the surgeon is usually required to temporarily relinquish the instrument to an assistant for dislodgement of the offending bone fragment.

A number of attempts have been made to circumvent the need to clear the jaws of a bone biting instrument during a surgical procedure. Most prior art attempts to allow repeated or multiple-bite operation of a rongeur deal with various approaches to storing cut fragments of bone within the instrument but away from the jaws of the instrument. For example, U.S. Pat. No. 3,902,498 to Niederer teaches a surgical cutting instrument having a storage recess within a cutting member, the storage recess includes an inlet opening for deposition of cut material therethrough, and a laterally directed discharge opening from which cut material may be subsequently removed at a point distant from the operation situs.

U.S. Pat. No. 4,722,338 to Wright et al. teaches a bone removing instrument in which bone chips or fragments severed from the patient are held and contained within a capturing cavity within the instrument until such time as the bone fragments may be purposely ejected therefrom.

U.S. Pat. No. 5,273,519 to Koros et al. teaches a rongeur surgical instrument wherein the tip of the movable shaft or cutting element includes a pressure relief hole or tunnel in which severed bone matter can be collected.

U.S. Pat. No. 5,385,570 and U.S. Pat. No. 5,582,618, both to Chin et al., teach a surgical cutting instrument wherein bone fragments severed from the patient are successively retained within the instrument as each successive bite is taken, the bone fragments being retained either within a recess located in the moveable cutting member, or within a collection chamber located in the handle.

U.S. Pat. No. 5,451,227 to Michaelson teaches a rongeur having a hollow collecting portion, located within the upper movable cutting assembly, for collecting and storing bone fragments therein.

A different approach is taught by Gambale for removing debris from the upper arm of a cutting instrument; thus, U.S. Pat. No. 5,569,258 to Gambale teaches a rongeur in which debris, such as bone fragments, retained within a concave recess at the cutting tip of the upper arm is removed by a flange projecting upwards from the distal end of the lower arm. A channel in the upper arm extends rearwardly from the cutting tip. The flange slides within the channel and beyond the concave recess, thereby ejecting debris from the concave recess of the upper arm as the upper arm moves rearwardly, away from the flange, in slidable engagement with the lower arm.

In contrast to the prior art cited above, the instant invention teaches a surgical bone biting instrument in which an ejecting unit, located within a recess in the stationary lower arm of the instrument, forcibly ejects debris lodged against the lower arm, as will be disclosed fully hereinbelow.

The above references are incorporated by reference herein where appropriate for appropriate teachings of additional or alternative details, features and/or technical background.

SUMMARY OF THE INVENTION

An object, therefore, of the invention is to provide a self-clearing bone biting surgical instrument which can be used repeatedly in uninterrupted fashion.

Another object of the invention is to provide a self-clearing bone biting surgical instrument wherein bone fragments or other debris may be forcibly ejected from the instrument as part of the normal operating procedure of the instrument.

Another object of the invention is to provide a self-clearing bone biting surgical instrument which includes an ejecting unit movable within a lower arm recess of the instrument to forcibly eject bone fragments from the instrument during routine operation of the instrument.

Another object of the invention is to provide a self-clearing bone biting surgical instrument which includes a flexible ejecting rod movable within a lower arm recess of the instrument, wherein the flexible ejecting rod is capable of forcibly ejecting bone fragments from the instrument during routine operation of the instrument.

Another object of the invention is to provide a self-clearing bone biting surgical instrument which includes an ejecting lever pivotally mounted within a lower arm recess of the instrument, wherein the ejecting lever is capable of pivoting within the lower arm recess to forcibly eject bone fragments from the instrument during routine operation of the instrument.

Another object of the invention is to provide a method for making a self-clearing bone biting surgical instrument, wherein the instrument includes an ejecting unit movable within a lower arm recess of the instrument, the ejecting unit being actuated during the normal operating procedure of the instrument in order to forcibly eject bone fragments or other debris from the instrument.

One advantage of the invention is that it provides a self-clearing bone biting instrument which can be used repeatedly without interruptions to clear debris from the lower arm of the instrument.

Another advantage of the invention is that it provides a self-clearing bone biting instrument in which any bone fragment(s) or debris lodged against the lower arm of the instrument may be dislodged after each bite.

Another advantage of the invention is that it provides a self-clearing bone biting instrument in which an ejecting unit forcibly ejects bone fragments from the instrument as part of the normal operating procedure of the instrument.

Another advantage of the invention is that it provides a method of making a selfclearing bone biting instrument, wherein the instrument includes an ejecting unit for forcibly ejecting bone fragments from the instrument after each bite has been taken by the instrument.

One feature of the invention is that it includes an ejecting unit movable within a lower arm of the instrument.

Another feature of the invention is that it includes an ejecting unit for forcibly ejecting bone fragments from the instrument after each bite of the instrument is taken.

Another feature of the invention is that it includes an ejecting unit for forcibly ejecting bone fragments from the instrument during normal operation of the instrument.

Another feature of the invention is that it provides a method for making a self-clearing rongeur, the rongeur having an ejecting unit movable within a lower arm recess of the lower arm of the instrument.

These and other objects, advantages, and features are accomplished by the provision of an instrument including: a lower arm; an upper arm, the upper arm and the lower arm reciprocally engageable for grasping a piece of material between the upper arm and the lower arm; and an ejecting unit movable with respect to the lower arm.

These and other objects, advantages, and features are accomplished by the provision of a self-clearing rongeur, including: a holding unit; an actuator pivotally coupled to the holding unit; an actuator return unit coupled to the actuator and to the holding unit; a lower arm coupled to the holding unit, the lower arm including a lower arm recess; an upper arm including an elbow and an upper arm recess, the upper arm actuated by the actuator, the upper arm reciprocating in slidable engagement with respect to the lower arm when the upper arm is actuated by the actuator; and an ejecting lever pivotally mounted within the lower arm recess.

These and other objects, advantages, and features are accomplished by the provision of a self-clearing rongeur, including: a holding unit; an actuator pivotally coupled to the holding unit; an actuator return unit coupled to the actuator and to the holding unit; a stationary lower arm coupled to the holding unit, the lower arm including a lower arm distal end, a lower arm engagement unit, and a lower arm recess; a movable upper arm including an upper arm recess and an upper arm engagement unit, the upper arm engagement unit cooperating with the lower arm engagement unit to hold the upper arm in slidable engagement with the lower arm, the upper arm actuated by the actuator, the upper arm reciprocating in slidable engagement with respect to the lower arm when the upper arm is actuated by the actuator; and an ejecting lever pivotally mounted within the lower arm recess.

These and other objects, advantages, and features are accomplished by the provision of a method for making a bone biting instrument, including the steps of: a) providing an upper arm of the instrument; b) providing a lower arm of the instrument, the lower arm including a lower arm recess; c) providing an ejecting unit; d) coupling the upper arm and the lower arm to each other; e) coupling the lower arm to an actuator; f) coupling the upper arm to the actuator; and g) mounting the ejecting unit within the lower arm recess.

These and other objects, advantages and features will become more apparent from the following description of embodiments thereof taken in conjunction with the accompanying drawings.

Additional advantages, objects, and features of the invention will be set forth in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

The invention will be described in detail with reference to the following drawings in which like reference numerals refer to like elements wherein:

FIG. 4A shows a face view of a lower arm of a bone biting instrument, as seen from above, according to one embodiment of the invention;

FIG. 4B shows a face view of an upper arm of a bone biting instrument, as seen from below, according to the invention;

DETAILED DESCRIPTION OF PREFERRED EMBODIMENTS

The instant invention provides a bone biting surgical instrument which includes an ejecting unit housed, at least in part, within the lower stationary arm of the instrument. According to one embodiment of the invention, the ejecting unit includes a flexible ejecting rod which moves distally within a lower arm recess to dislodge tissue from the foot plate each time the upper arm of the instrument moves proximally during normal operation of the instrument. According to another embodiment of the invention, the ejecting unit includes a rigid ejecting rod having a head portion; the rigid ejecting rod moves proximally, in concert with the upper arm, within a lower arm recess to dislodge tissue from the foot plate each time the instrument is operated. According to yet another embodiment of the invention, the ejecting unit includes a pivotally mounted ejecting lever; a shaft portion of the ejecting lever is urged into alignment with the longitudinal axis of the lower arm as the upper arm moves rearwardly to a sufficient extent beyond the location of the pivot point of the lever, thereby allowing a boot portion of the ejecting lever to forcibly eject debris lodged against the distal end of the lower arm.

Figure 1:
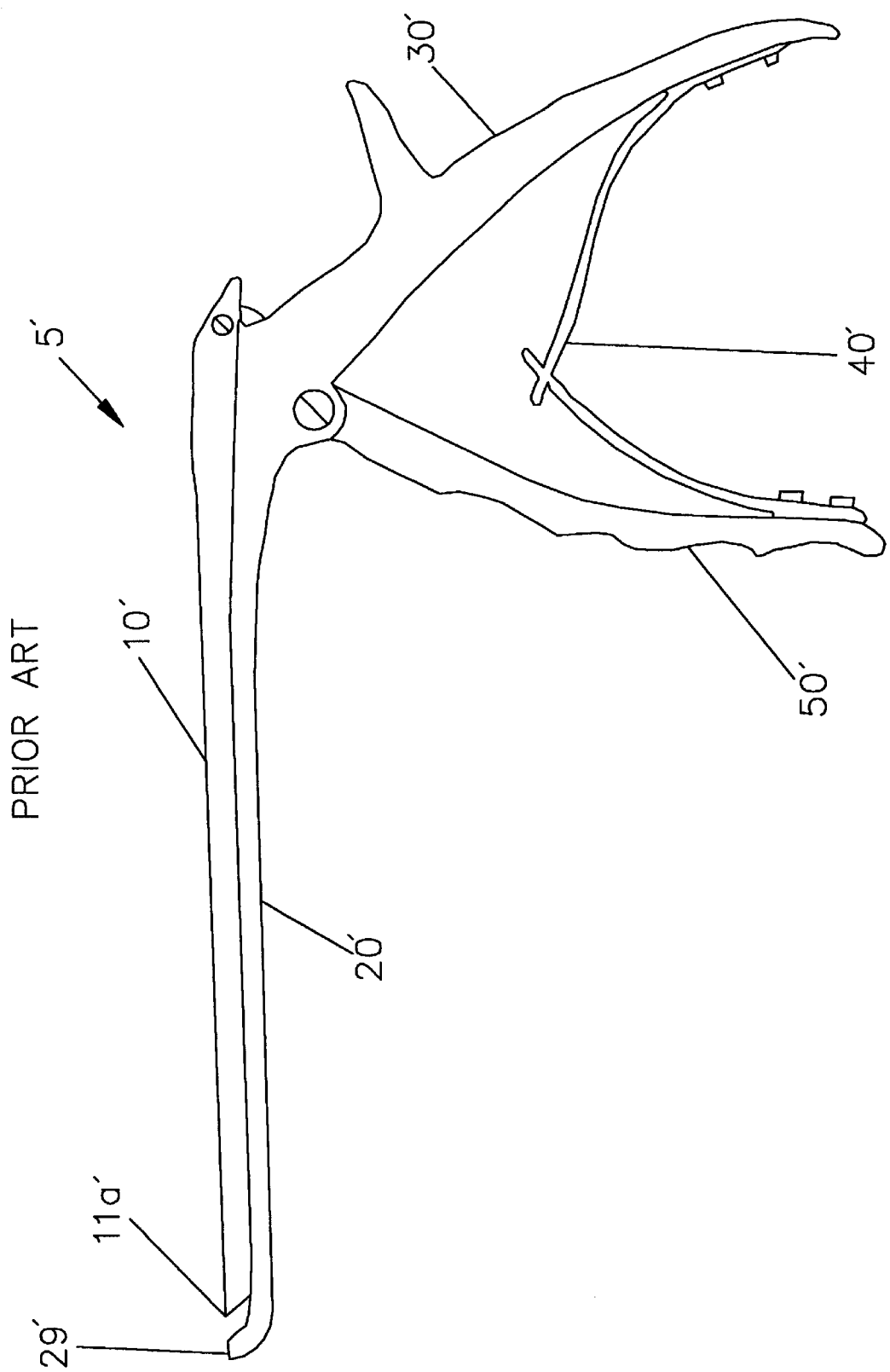
FIG. 1 represents a prior art bone biting instrument.

Referring now to the drawings, FIG. 1 represents a bone biting instrument 5' of the prior art which includes a stationary lower bar 20' having a foot plate or anvil 29' located at its distal end and an integral handle 30'; a moveable upper bar 10' having a cutting tip 11a' located at its distal end for forcible engagement with foot plate or anvil 29' to effect cutting or punching of tissue positioned between foot plate 29' and cutting tip 11a'; an actuator 50', pivotally coupled to handle 30' for actuating reciprocal motion of the upper arm vis a vis lower arm 20'; and an actuator return unit 40', typically in the form of a spring assembly. Cutting tip 11a' is forcibly engaged or compressed against foot plate 29' by way of actuator 50'. Upper arm 10' may be held in slidable engagement against lower arm 20' by various means, for example, by a complementary tongue and groove mechanism (not shown), such as is well known in the art.

Figure 2:
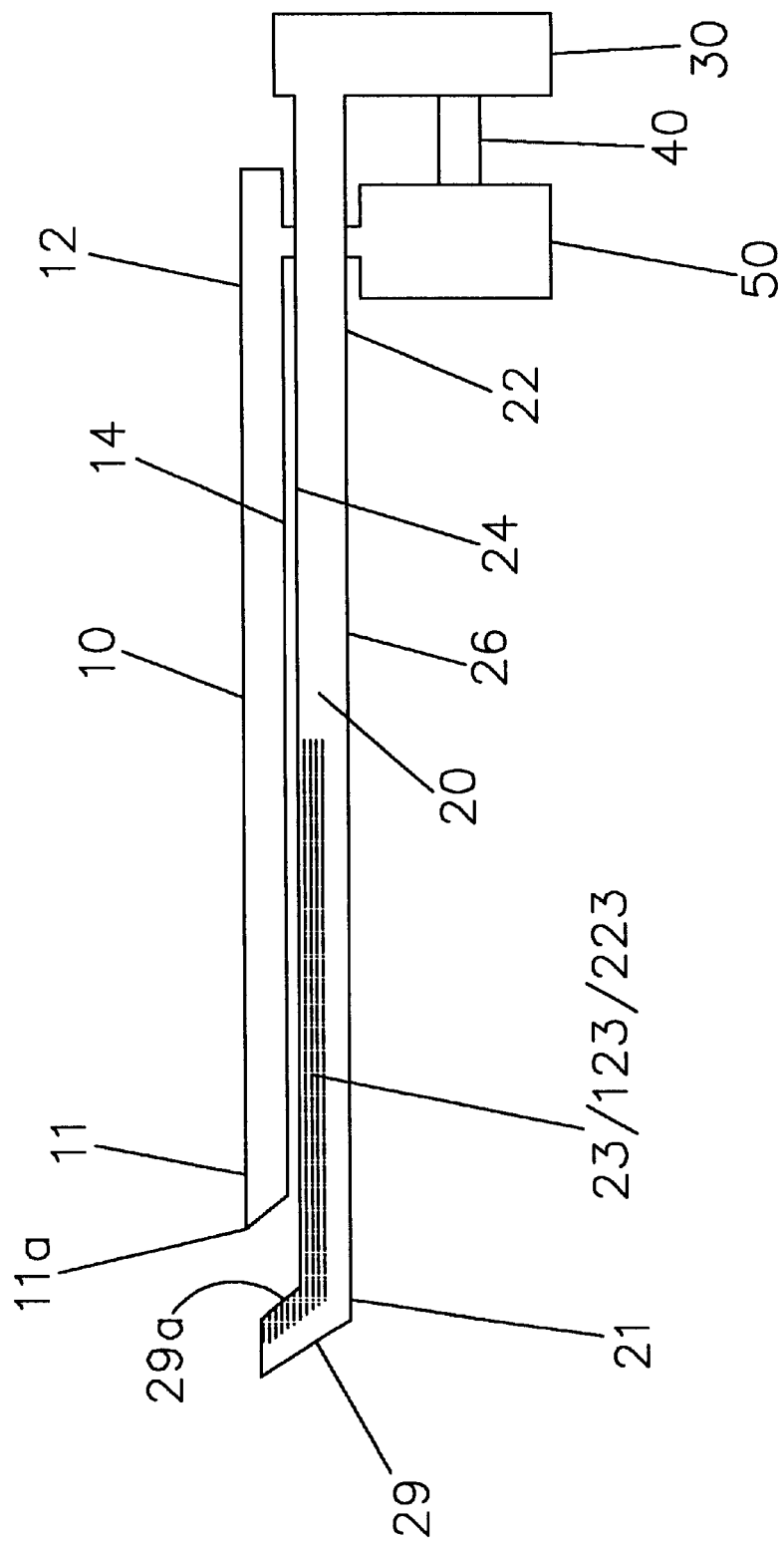
FIG. 2 shows a side view of a bone biting instrument in schematic form, with the ejecting unit omitted for the sake of clarity, according to one embodiment of the invention.

FIG. 2 shows a bone biting instrument 5, according to one embodiment of the invention. Instrument 5 of the instant invention may include, in its various embodiments, at least some of the features described hereinabove with respect to FIG. 1. Instrument 5 further includes additional elements and features as will now be fully described.

Instrument or rongeur 5 of FIG. 2, according to the instant invention, includes a moveable upper arm 10; a stationary lower arm 20; a handle or holding unit 30 coupled to, or integral with, lower arm 20; an actuator 50 coupled to lower arm 20 and to upper arm 10 for actuating reciprocal motion of upper arm 10 with respect to lower arm 20; and an actuator return unit 40 coupled to actuator 50 and holding unit 30. Tissue such as bone or other material may be grasped between the jaws of instrument 5, i.e. between the distal end of upper arm 10 and foot plate 29, by actuating actuator 50. Severing of bone or other tissue is enacted via the cutting tip 11a of upper arm 10 being forcibly engaged against tissue positioned on or against cutting surface 29a of foot plate 29.

Figure 6A:
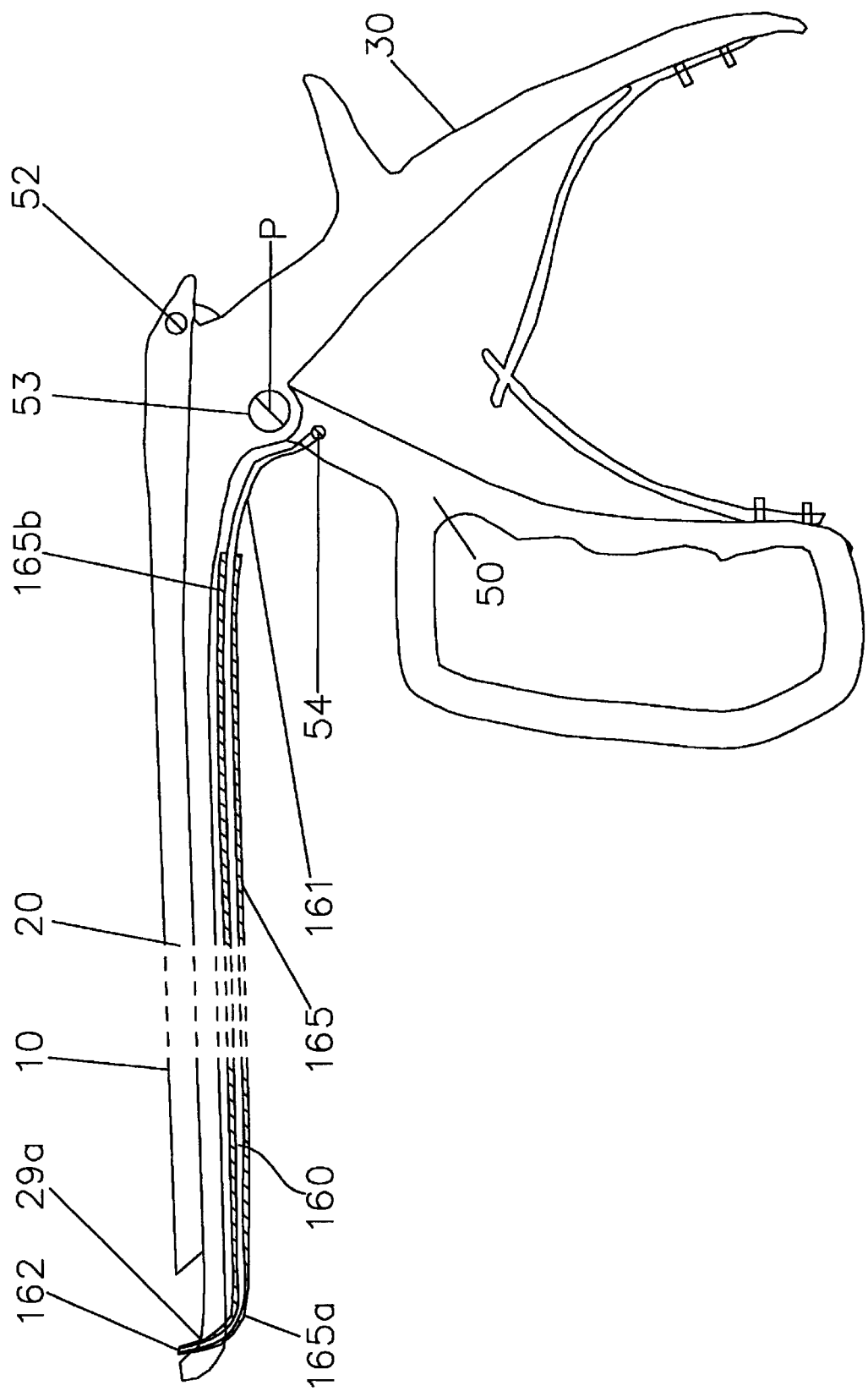
FIG. 6A shows a side view of a bone biting instrument with the jaws of the instrument in the open position, and showing the attachment of the flexible ejecting rod to the actuator at a location inferior to the pivot point, according to another embodiment of the invention.
Figure 7A:
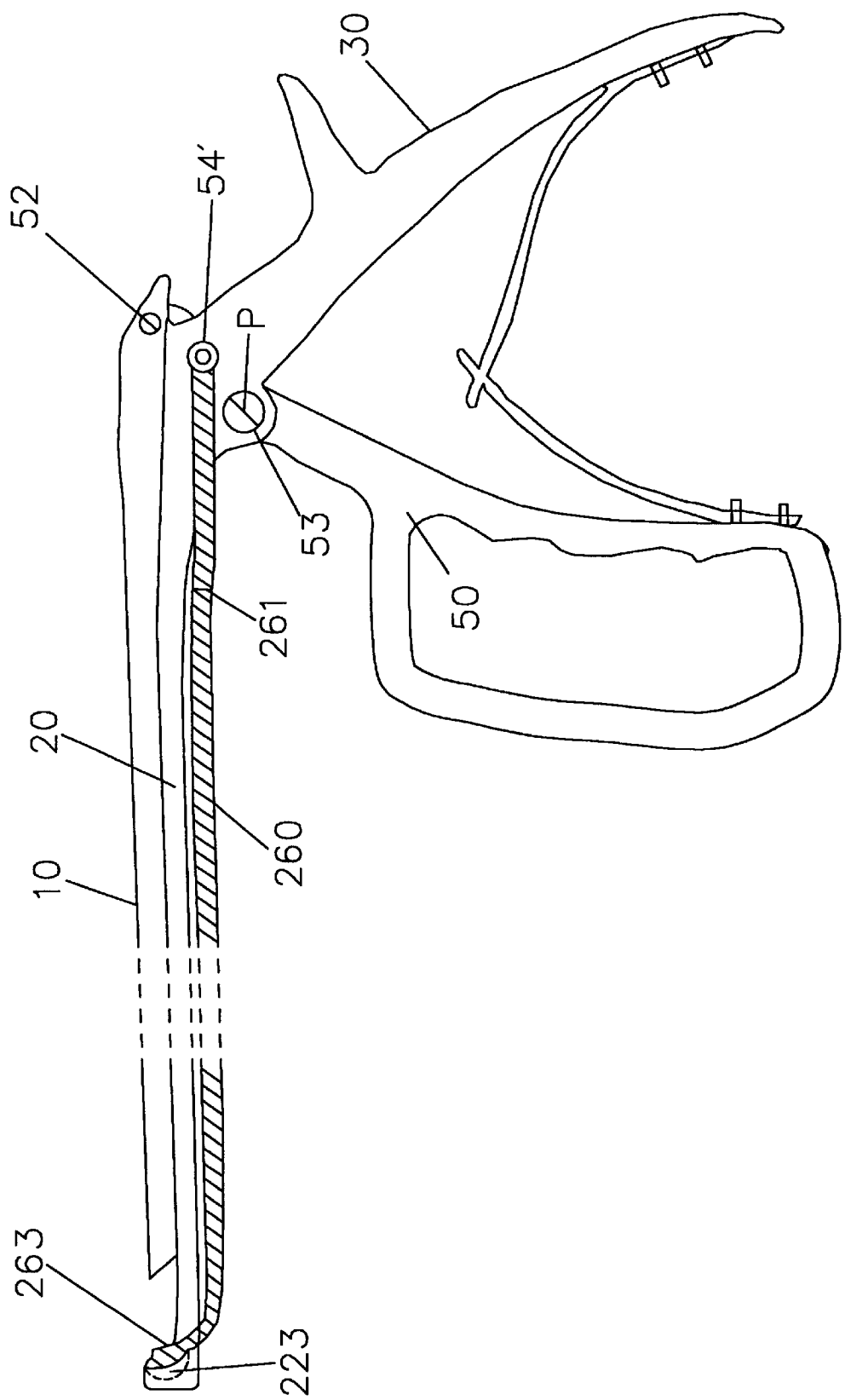
FIG. 7A shows a side view of a bone biting instrument with the jaws of the instrument in the open position, and showing the attachment of the rigid ejecting rod to the actuator at a location superior to the pivot point, according to another embodiment of the invention.

Lower arm 20 includes a lower arm recess 23/123/223 FIGS. 4A, 6A, 7A) therein, the latter housing at least a portion of an ejecting unit 6. Lower arm recess 23/123/223 of various embodiments of the invention are represented generically in FIG. 2, while ejecting unit 6 is omitted from FIG. 2 for the sake of clarity. The nature of the lower arm recess (either 23, 123, or 223) varies according to different embodiments of the invention, as will be described fully hereinbelow. Ejecting unit 6 may include either an ejecting lever (FIG. 3A), a flexible ejecting rod (FIG. 6A), or a rigid ejecting rod (FIG. 7A), according to various embodiments of the invention.

Upper arm 10 may include an upper arm engagement unit (not shown) for cooperation with a complementary lower arm engagement unit (also not shown) of lower arm 20. Upper arm and lower arm engagement units cooperate to hold upper arm 10 in slidable engagement with the lower arm 20. (A gap is shown between interior edge 14 and interior edge 24 in FIG. 2 for the sake of clarity only and an actual embodiment may not have such a gap.) Upper arm and lower arm engagement units may take the form of several mechanisms well known in the art, for example, one or more tongues on upper arm 10 and the same number of complementary grooves on lower arm 20. According to certain embodiments of the invention, upper arm 10 may also include an upper arm recess 13 (FIG. 3B).

Figure 3A:
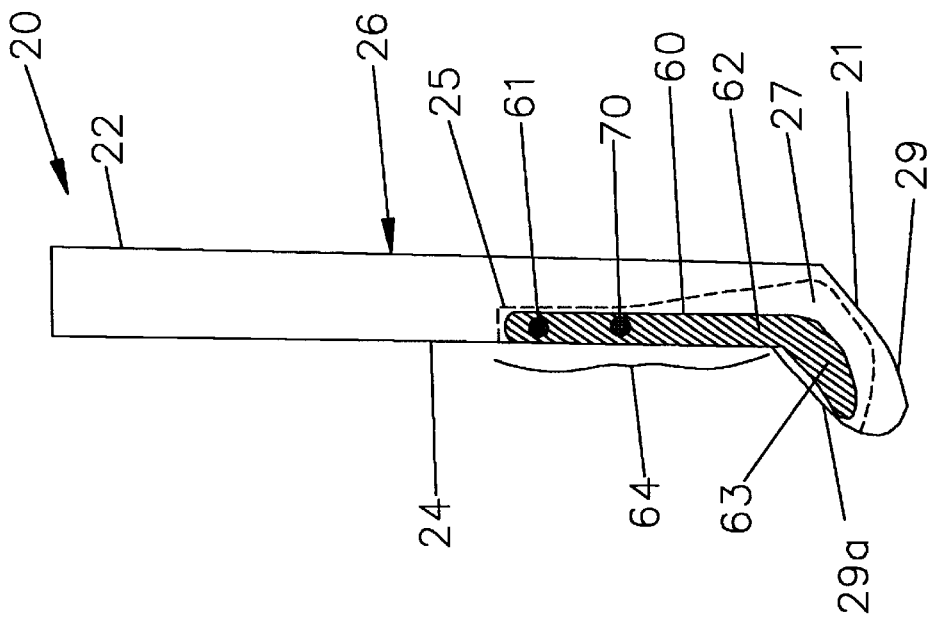
FIG. 3A shows a sectional view of a lower arm of a bone biting instrument including an ejecting lever, according to one embodiment of the invention.

FIG. 3A is a sectional view of lower arm 20 of bone biting instrument 5, according to one embodiment of the invention.

Lower arm 20 includes a proximal end 22 and a distal end 21, the latter including an angled portion in the form of a foot plate or anvil 29. Lower arm 20 further includes lower arm recess 23 located longitudinally within lower arm 20 towards lower arm distal end 21. FIG. 3A indicates the relative position of lower arm recess 23 with respect to distal end 21. Lower arm recess 23 is of variable depth being deepest at lower arm recess inferior portion 27 where it extends into foot plate 29. Ejecting lever 60 is pivotally mounted within lower arm recess 23. According to a preferred embodiment, ejecting lever 60 is shaped like a hockey stick and includes a boot portion 63 extending from ejecting lever inferior part 62 of shaft 64. Preferably, ejecting lever 60 is pivotally mounted within lower arm recess 23 by pivot post 70. Pivot post 70, and therefore the pivot point of ejecting lever 60, is located within shaft 64 towards ejecting lever superior part 61. When instrument 5 is fully assembled, pivot post 70 allows ejecting lever 60 to pivot within the confines of upper arm recess 13 and lower arm recess 23, including lower arm recess inferior portion 27. Lower arm recess superior portion 25 is sufficiently shallow so as to prevent boot 63 from pivoting beyond the confines of lower arm recess inferior portion 27 at cutting surface 29a.

Figure 3B:
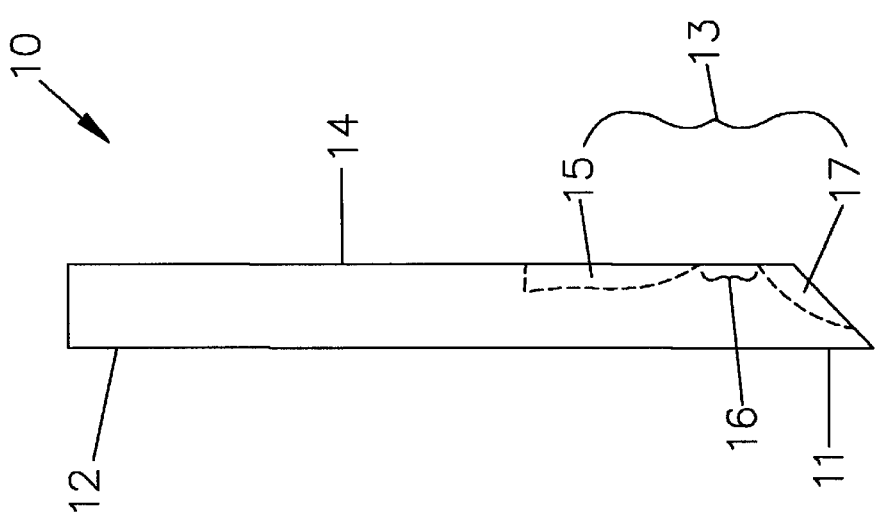
FIG. 3B shows a side view of an upper arm of a bone biting instrument, according to the invention.

FIG. 3B shows a side view of upper arm 10 of bone biting instrument 5, according to one embodiment of the invention. Upper arm 10 includes elbow 16 and upper arm recess 13. Upper arm recess 13 may be of variable depth, having upper arm recess superior portion 15 and upper arm recess inferior portion 17. Elbow 16 lies between superior portion 15 and inferior portion 17, at which location upper arm recess 13 may effectively terminate or, viewed alternatively, have a depth of zero. Stated differently, elbow 16 may be flush, or aligned, with upper arm interior edge 14. Upper arm recess superior portion 15 allows ejecting lever superior portion 61 to pivot therein, thereby permitting boot 63 to pivot into an open position with respect to cutting surface 29a. (FIG. 5B). Elbow 16 should extend close to upper arm interior edge 14 and flush therewith in a preferred embodiment. Elbow 16 engages against ejecting lever superior portion 61 as upper arm 10 reciprocates rearwardly with respect to lower arm 20. In particular, as elbow 16 engages against ejecting lever 60 at a point proximal to pivot post 70, shaft 64 of ejecting lever 60 is forced into alignment with lower arm interior edge 24, and concomitantly boot 63 is forced to a closed position with respect to cutting surface 29a (FIG. 5A), i. e. to a position adjacent to cutting surface 29a. Consequently, ejecting lever 60 is forced to pivot from an open position to a closed position as upper arm 10 reciprocates in slidable engagement with lower arm 20.

According to one embodiment of the invention, upper and lower arm engagement units may include a pair of tongues (not shown) on upper arm 10, and the pair of tongues may each lie external (bilaterally) to upper arm recess 13, and a pair of complementary grooves (also not shown) which may each lie external to lower arm recess 23, such that neither the pair of tongues nor the pair of grooves interfere with the capability of ejecting lever 60 to pivot within upper arm recess 13 or lower arm recess 23 (refer to FIGS. 3A, 3B).

FIG. 4A is a face view of lower arm 20 of bone biting instrument 5, as seen from above, and shows ejecting lever 60 mounted within lower arm recess 23 by pivot post 70. Ejecting lever 60 is narrower than lower arm recess 23 so that ejecting lever 60 can pivot freely within recess 23 when a force is applied to ejecting lever superior part 61 of shaft 64 by elbow 16.

FIG. 4B is a face view of upper arm 10 of bone biting instrument 5, as seen from below, and shows the relative location of upper arm recess 13 which lies substantially in a central position parallel to the longitudinal axis of upper arm 10. Upper arm recess 23 is preferably wider than ejecting lever 60 so that distal end 61 of ejecting lever 60 can be temporarily accommodated within upper arm recess superior portion 15 when boot 63 of ejecting lever 60 is forced into the open position (FIG. 5B) by the presence of debris lodged against cutting surface 29a of foot plate 29.

According to one embodiment of the invention, instrument 5 may include a mechanism (not shown), such as a spring, to retain ejecting lever 60 in the closed position until ejecting lever 60 is forced into the open position by the presence of a bone fragment, etc., lodged against cutting surface 29a.

Figure 5A:
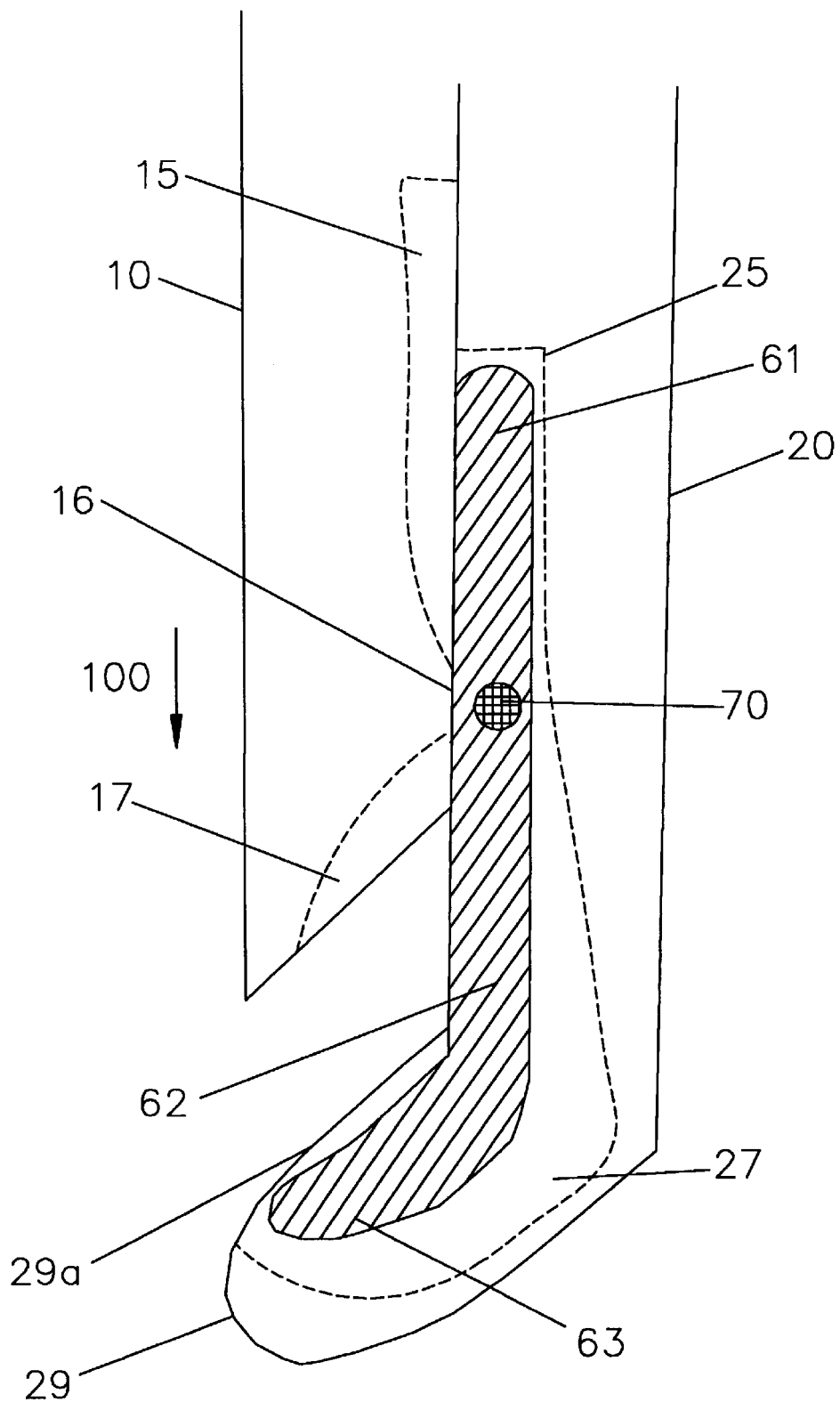
FIG. 5A shows the distal end of a bone biting instrument with the upper arm of the instrument moving towards the distal end of the lower arm, with the arms of the instrument free from debris and the shaft of the ejecting lever aligned with the longitudinal axis of the lower arm, according to one embodiment of the invention.
Figure 5B:
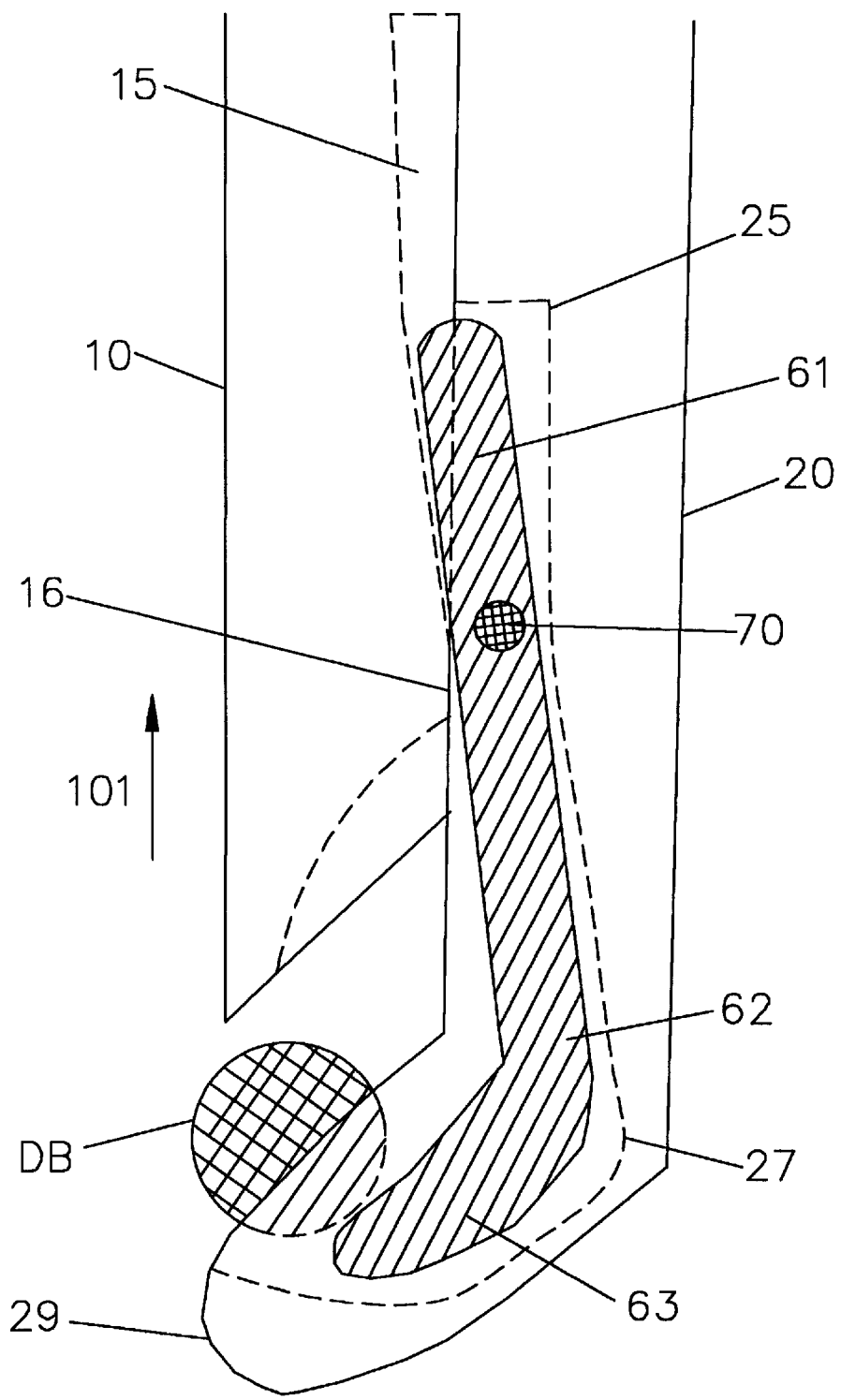
FIG. 5B shows the distal end of a bone biting instrument shortly after the upper arm of the instrument has begun to move away from the distal end of the lower arm, with the shaft of the ejecting lever forced out of alignment with the longitudinal axis of the lower arm by a bone fragment lodged against the lower arm recess inferior portion adjacent to the boot portion of the ejecting lever, according to the invention.

FIG. 5A shows the distal end of bone biting instrument 5 with upper arm 10 moving towards foot plate 29 as indicated by the arrow labeled 100. Foot plate 29 is free from debris, and ejecting lever 60 is in the closed position; i. e. shaft 64 is aligned with lower arm interior edge 24 (FIG. 3A), while boot 63 lies adjacent to cutting surface 29a. Such a situation exists prior to taking a bite of bone with instrument 5. As described previously, ejecting lever 60 is pivotally mounted by pivot post 70 within lower arm 20. Pivot post 70 acts as the fulcrum for the lever action of ejecting lever 60. According to the invention, pivot post 70 may also serve as a resilience mechanism to prevent unnecessary movement of ejecting lever 60 in the absence of a force being applied thereto, either by elbow 16 or the "workpiece" (i. e. bone or tissue).

FIG. 5B shows the distal end of bone biting instrument 5 in a situation shortly after taking a bite of bone with instrument 5. Upper arm 10 is shown moving away from foot plate 29 as indicated by the arrow labeled 101. Debris DB, such as a bone fragment, is lodged against cutting surface 29a of foot plate 29, thereby forcing ejecting lever 60 into the open position; i.e. shaft 64 is out of alignment with lower arm interior edge 24 (FIG. 3A) such that ejecting lever superior part 61 pivots into upper arm recess superior portion 15, while boot 63 lies away from cutting surface 29a in the distant confines of lower arm recess inferior portion 27.

Figure 5C:
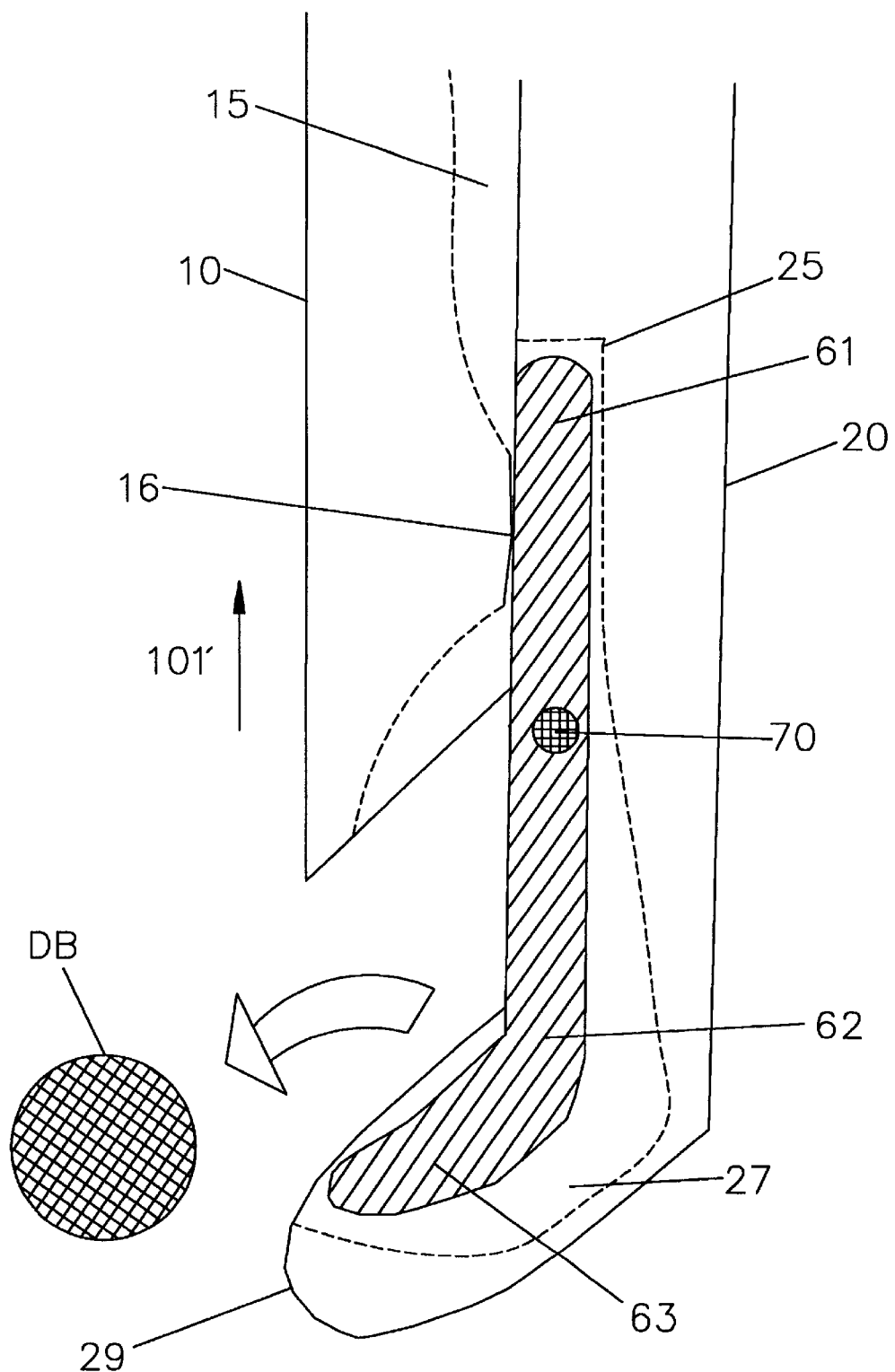
FIG. 5C shows the distal end of a bone biting instrument with the upper arm of the instrument having moved away from the distal end of the lower arm, and the shaft of the ejecting lever having been moved into alignment with the longitudinal axis of the lower arm by a force applied to the shaft of the ejecting lever at a location proximal to the pivot point of the ejecting lever, according to the invention.

FIG. 5C shows the distal end of bone biting instrument 5 with upper arm 10 moving away from foot plate 29 as indicated by the arrow labeled 101'. As elbow 16 of upper arm 10 continues to move away from foot plate 29 to a point proximal of pivot post 70, elbow 16 forcibly engages ejecting lever superior portion 61 thereby forcing ejecting lever 60 to occupy the closed position. As a result, debris DB, once lodged against cutting surface 29a, is dislodged or forcibly ejected therefrom via the lever action exerted by ejecting lever 60, specifically by boot 63 being moved to a position adjacent to cutting surface 29a. According to the series of events described in relation to FIGS. 5A–5C, the arms of instrument 5 are self-cleared of debris, after each bite, by the normal operating procedure of instrument 5. Consequently, the surgeon may take the requisite number of bites to complete a given surgical procedure without undue interruption.

FIG. 6A shows a bone biting instrument 5 according to the invention with the jaws of the instrument in the open position. Lower arm 20 together with integral holding unit 30 is coupled to actuator 50 at pivot point P by a pivot pin 53. Upper arm 10 is coupled to actuator 50 at a location superior to pivot point P by an upper arm coupling pin 52. Upper arm 10 moves distally towards foot plate 29 when actuator 50 is urged towards holding unit 30. Flexible ejecting rod 160 is secured to actuator 50 at a location inferior to pivot point P via securing pin 54. Flexible ejecting rod 160 therefore moves counter to upper arm 10 when actuator 50 is urged towards holding unit 30, i. e. flexible ejecting rod 160 moves distally to dislodge debris lodged against cutting surface 29*a*. According to a currently preferred embodiment, proximal portion 161 of ejecting rod 160 may lie external to lower arm 20 and may be housed within a tubular housing 165. Tubular housing 165 may extend to various extents along flexible ejecting rod 160; housing 165 at its distal end 165*a* may terminate adjacent to lower arm distal end 21, while at its proximal end 165*b* housing 165 may terminate adjacent to actuator 50. Tubular housing 165 may be considered, at least from a functional standpoint, as an extension of lower arm recess 123.

Figure 6B:
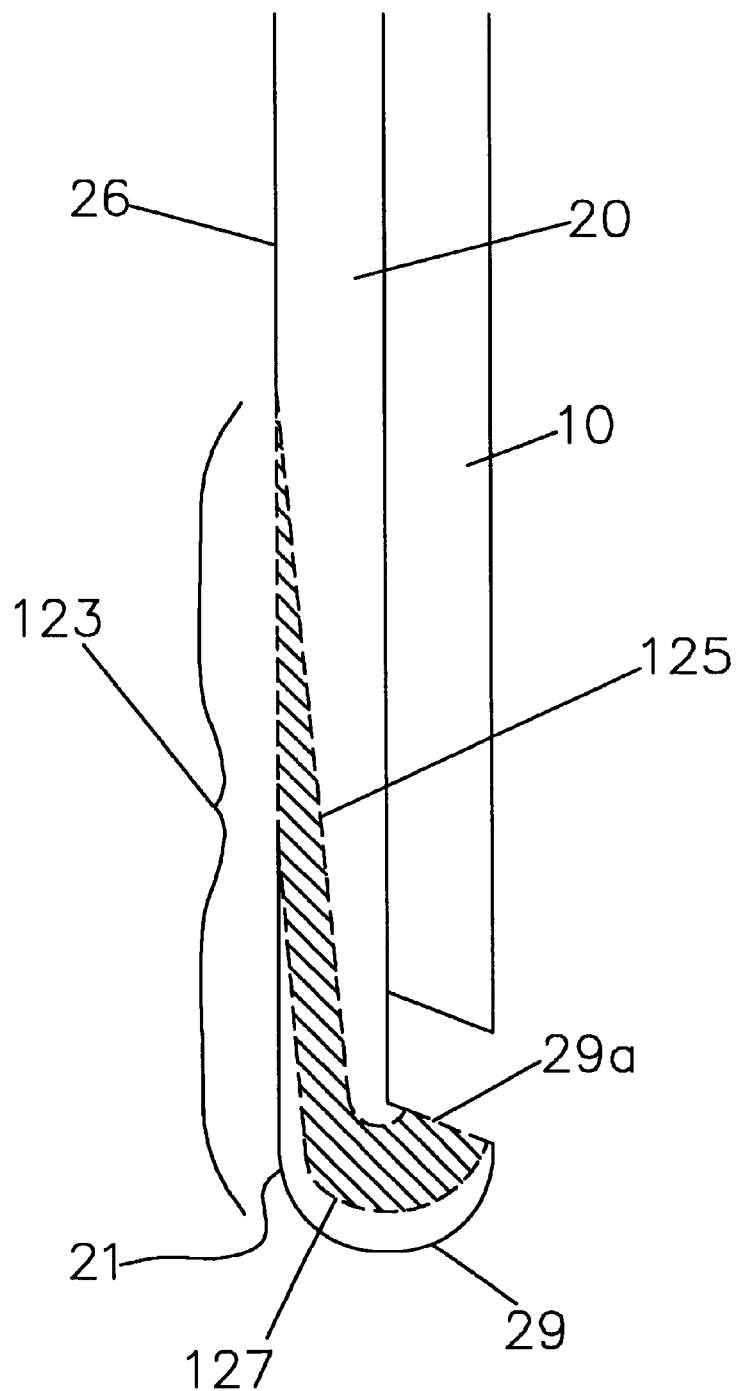
FIG. 6B shows a side view of a bone biting instrument with the jaws of the instrument in the partially open position and the ejecting unit omitted for the sake of clarity.
Figure 6C:
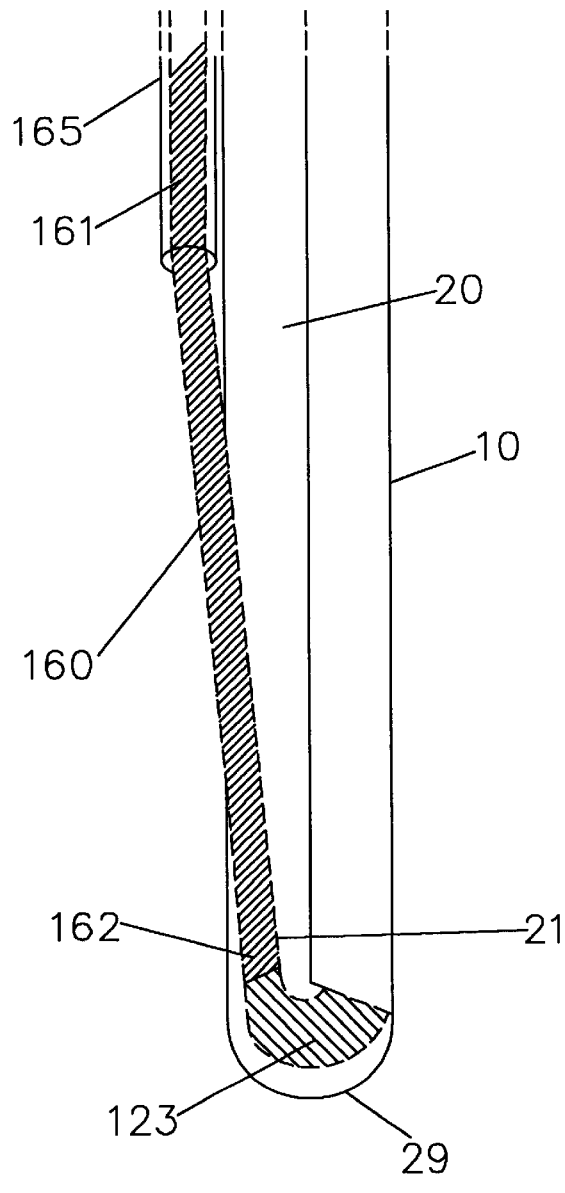
FIG. 6C shows a side view of a bone biting instrument with the jaws of the instrument in the closed position and the flexible ejecting rod in a recessed position, according to the invention.
Figure 6D:
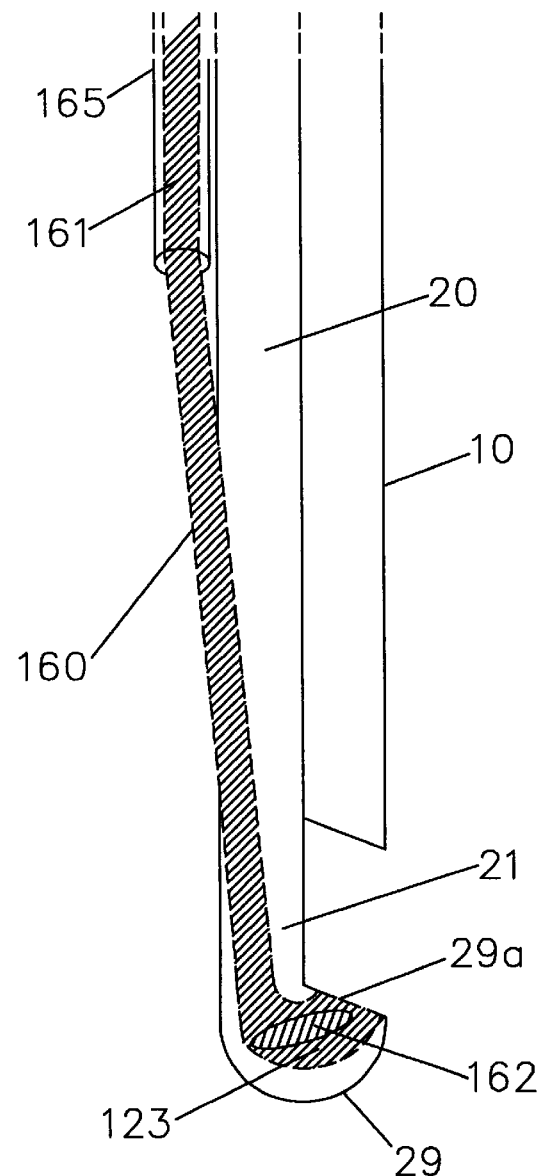
FIG. 6D shows a side view of a bone biting instrument with the jaws of the instrument in the open position, and the distal end of the flexible ejecting rod is substantially in alignment with the cutting surface of the lower arm, according to the invention.

FIG. 6B shows the distal end of bone biting instrument 5 according to the invention, with the jaws of instrument 5 partially open. Lower arm 20 includes a lower arm recess 123 within distal end 21 of lower arm 20. Lower arm recess 123 includes a proximal portion 125 and a distal portion 127. Proximal portion 125 may be substantially cylindrical and has a diameter somewhat larger than the diameter of flexible ejecting rod 160 (FIGS. 6C, 6D). Lower arm recess 123 may extend from lower arm exterior edge 26 to anvil 29 where distal portion 127 follows a curved path to open at cutting surface 29*a*. Flexible ejecting rod 160 is omitted from FIG. 6B for the sake of clarity only.

FIG. 6C shows the distal end of bone biting instrument 5 according to the invention, wherein the jaws of the instrument are in the closed position and distal end 162 of flexible ejecting rod 160 is accommodated in a recessed position within lower arm recess 123. Flexible ejecting rod 160 includes a proximal portion 161 which may lie external to lower arm 20. Distal portion 162 of rod 160 is responsible for ejecting debris lodged against cutting surface 29*a*.

With reference to FIG. 6D, proximal portion 161 of flexible ejecting rod 160 may be coupled to actuator 50 at a point below, or inferior to, pivot point P (FIG. 6A) such that when upper arm 10 moves proximally to open the bone biting instrument, distal end 162 of flexible ejecting rod 160 is urged distally within lower arm recess 123 to the extent that distal end 162 is at least substantially in alignment with cutting surface 29*a*. Thus, flexible ejecting rod 160 moves counter, or substantially in an opposite direction, to upper arm 10 when upper arm 10 is actuated by actuator 50. In this way, debris is removed from cutting surface 29*a* each time instrument 5 is moved to the open position during normal operating procedures.

Figure 6E:
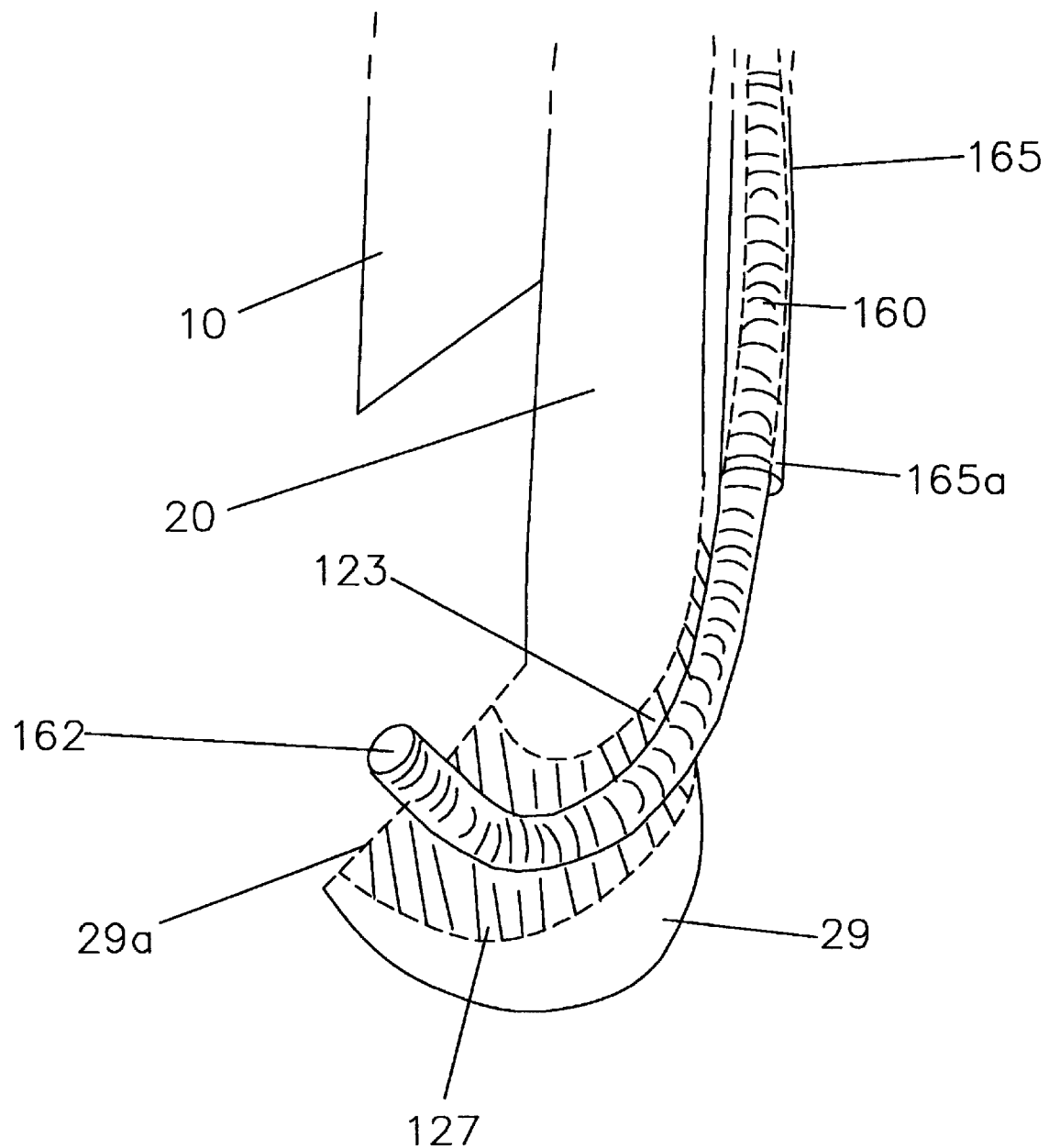
FIG. 6E shows a detailed side view of the distal part of a bone biting instrument with the jaws of the instrument in the open position, and the distal end of the flexible ejecting rod protruding from the cutting surface of the lower arm, according to one embodiment of the invention.

FIG. 6E shows a side view of the distal portion of bone biting instrument 5 with the jaws of the instrument in the open position. Flexible ejecting rod 160 is housed partially within tubular housing 165, and extends through distal portion 127 of lower arm recess 123. According to one embodiment of the invention, as the jaws of instrument 5 are moved to the open position, i. e. as upper arm 19 moves proximally, flexible ejecting rod 160 may be urged distally to such an extent that distal end 162 of ejecting rod 160 may protrude beyond cutting surface 29*a*, thereby serving to dislodge debris from cutting surface 29*a*.

FIG. 7A shows a side view of bone biting instrument 5 according to the invention with the jaws of the instrument in the open position. Lower arm 20 together with integral holding unit 30 is coupled to actuator 50 at pivot point P by pivot pin 53. Upper arm 10 is coupled to actuator 50 at a point superior to pivot point P by an upper arm coupling pin 52. Upper arm 10 moves distally towards foot plate 29 when actuator 50 is urged towards holding unit 30. A rigid ejecting rod 260 is also secured to actuator 50 at a point superior to pivot point P, but inferior to upper arm coupling pin 52, via securing pin 54'. Rigid ejecting rod 160 therefore moves in tandem with upper arm 10 when actuator 50 is urged towards holding unit 30, but with a shorter throw than upper arm 10. The actual throw, or maximum displacement, of rigid ejecting rod 160 effected by actuator 50 can be varied according to the position of securing pin 54' with respect to pivot point P. Rigid ejecting rod 160 may be secured to actuator 50 either internal (e. g. centrally) or external to holding unit 30.

Figure 7B:
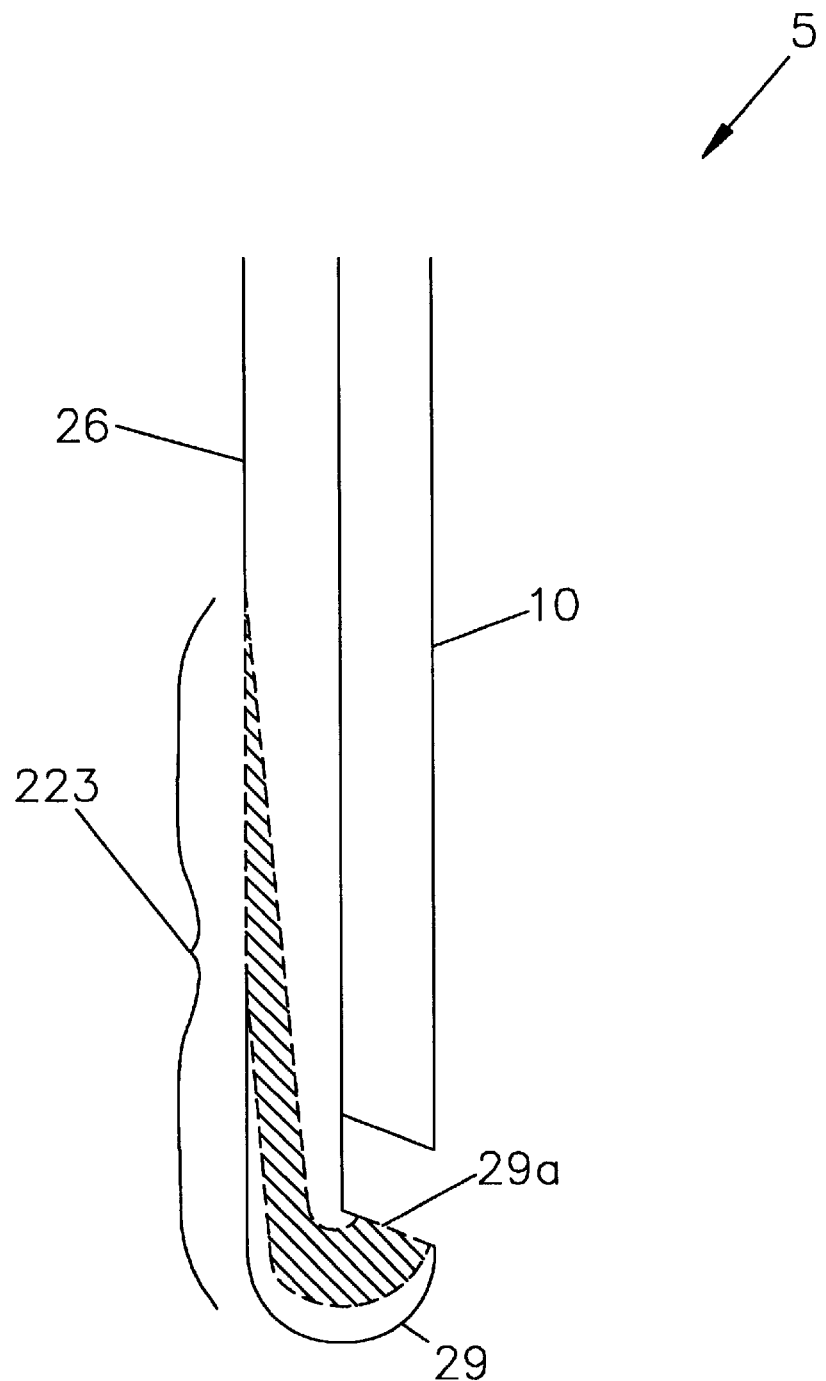
FIG. 7B shows a side view of a bone biting instrument according to the invention, with the jaws of the instrument in the partially open position, and the ejecting unit omitted for the sake of clarity.

FIG. 7B shows the distal end of bone biting instrument 5 according to the invention, with the jaws of the instrument in the partially open position. Lower arm 20 includes a lower arm recess 223 within lower arm distal end 21. Lower arm recess 223 extends from lower arm exterior edge 26 into and throughout foot plate 29. Ejecting unit 6 is omitted from FIG. 7B for the sake of clarity only.

Figures 7C, 7D:
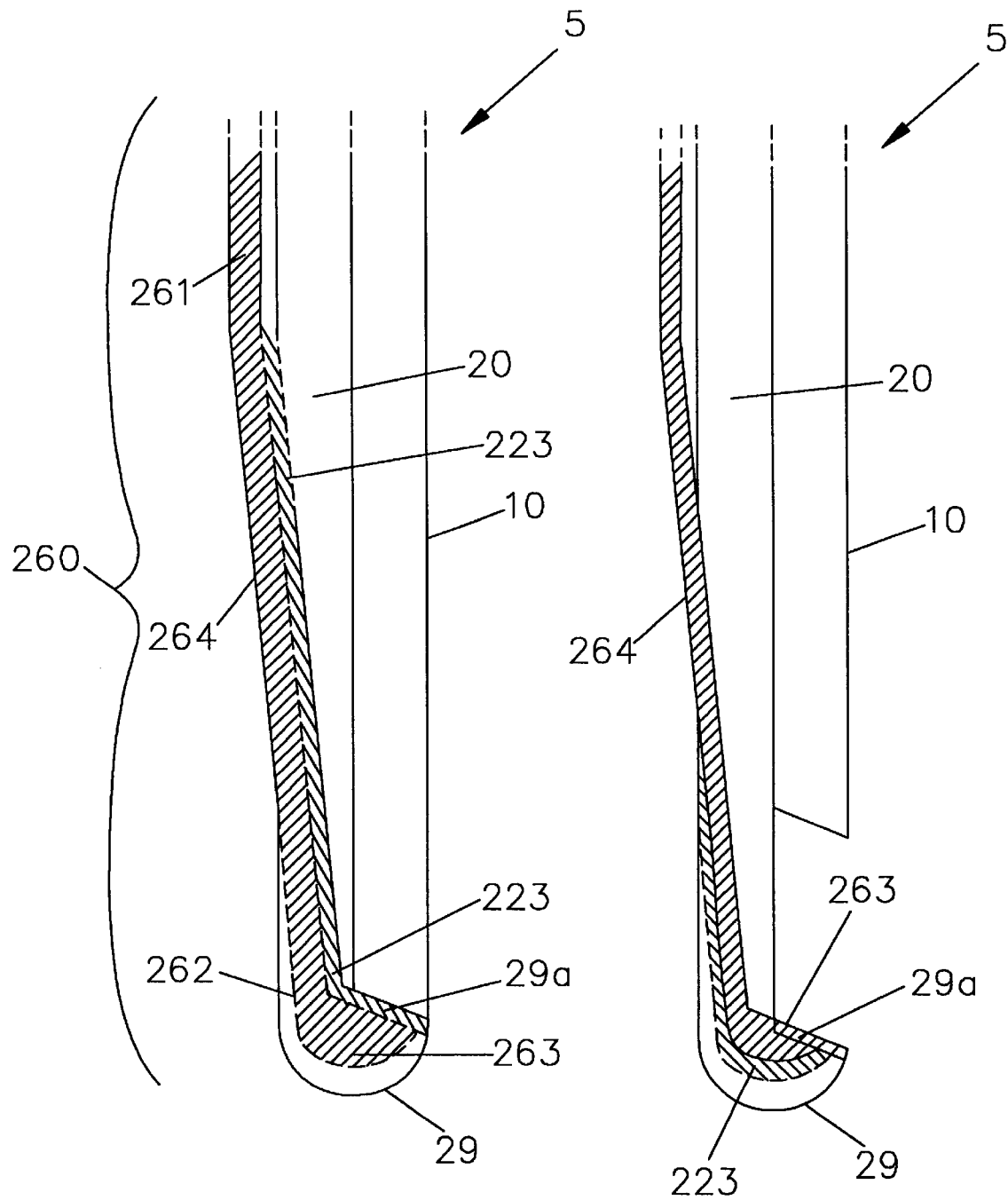
FIG. 7C shows a side view of a bone biting instrument with the jaws of the instrument in the closed position and the rigid ejecting rod in a recessed position, according to the invention.
FIG. 7D shows a side view of a bone biting instrument with the jaws of the instrument in the open position, and the head portion of the rigid ejecting rod protruding from the cutting surface of the lower arm, according to the invention.

With reference to FIG. 7C, lower arm recess 223 accommodates an ejecting unit 6 in the form of a rigid ejecting rod 260 having a golf club shape. Rigid ejecting rod 260 includes a shaft 264 having a proximal end 261 and a distal end 262 and further including a head portion 263 at distal end 262. The proximal end 261 of shaft 264 may be coupled to actuator 50 such that rigid ejecting rod 260 including head portion 263 moves in tandem (i.e. at the same time and in the same general direction) with upper arm 10. According to an alternative embodiment, proximal end 261 may be coupled directly to upper arm 10.

When bone biting instrument 5 is in the closed position, as shown in FIG. 7C, head portion 263 is entirely housed or recessed within lower arm recess 223. As upper arm 10 moves proximally to open the bone biting instrument, as shown in FIG. 7D, head portion 263 also moves proximally such that head portion 263 at least partially protrudes from within anvil 29 at cutting surface 29*a*, thereby dislodging any debris lodged against cutting surface 29*a*. Thus, as the jaws of the instrument are opened by actuator 50, rigid ejecting rod 20 moves proximally within lower arm recess 223 to dislodge debris lodged against cutting surface 29*a*. In this way, debris is once again removed from cutting surface 29*a* each time instrument 5 is moved to the open position during normal operating procedures.

During operation of instrument 5, according to the instant invention, bone fragments are dislodged at a specific point in the operation cycle of the instrument, namely as upper arm 10 moves in a proximal direction away from foot plate 29. In this way, instrument 5 can be removed from the operation situs at the time of dislodgement thereby easily avoiding contamination of the operation situs with unwanted tissue fragments. As appropriate, a sample of bone or other tissue may be purposely and specifically ejected to a suitable receptacle, by the normal action of instrument 5, for biopsy purposes, etc.

Figure 8:
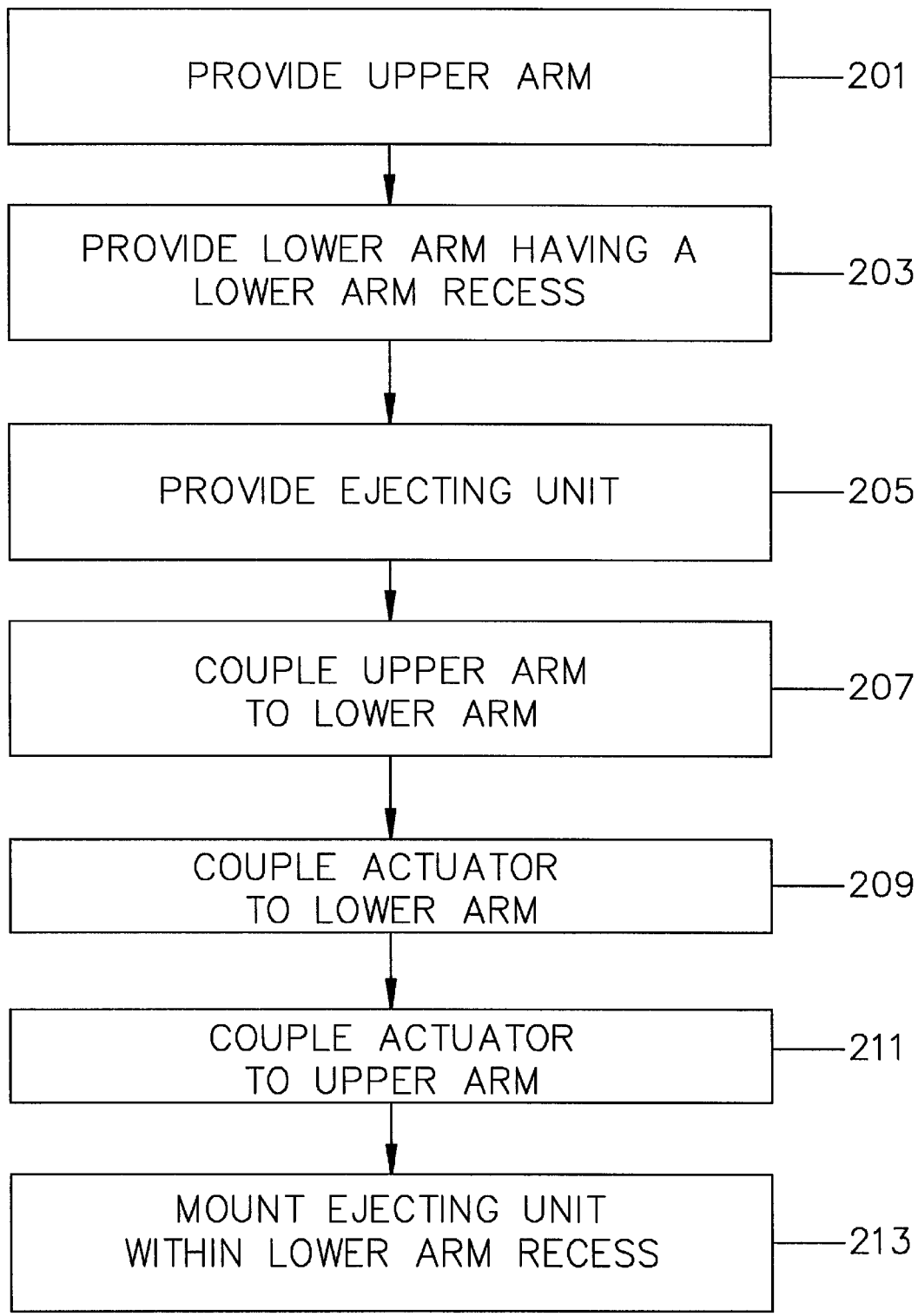
FIG. 8 summarizes the steps involved in a method for making a bone biting instrument, according to another embodiment of the invention.

FIG. 8 schematically represents a series of steps involved in a process for making a bone biting instrument, according to another embodiment of the invention. Step 201 involves providing an upper arm of the bone biting instrument. According to one embodiment of the invention, the upper arm may include an elbow and an upper arm recess. The upper arm recess may be located substantially centrally within the upper arm and substantially parallel to the longitudinal axis of the upper arm. According to one embodiment of the invention, the upper arm provided in step 201 includes a recess of variable depth having an upper arm recess superior portion and an upper arm recess inferior portion, with an elbow located therebetween. The upper arm provided in step 201 may further include a suitable upper arm engagement unit.

Step 203 involves providing a lower arm having a lower arm recess located therein. The lower arm provided in step 203 may include an integral handle or holding unit at its proximal end, and a foot plate at the distal end of the lower arm, the lower arm recess extending within the foot plate. According to one embodiment, the lower arm provided in step 203 includes a lower arm recess, extending from the lower arm exterior edge to the foot plate cutting surface, for accommodating a flexible ejecting rod. The proximal portion of the flexible ejecting rod may be at least partially housed within a tubular housing which may lie external to the lower arm. From a functional standpoint, the tubular housing may be considered as an extension of the lower arm recess. According to another embodiment, the lower arm provided in step 203 includes a lower arm recess extending from the lower arm exterior edge to the foot plate cutting surface, for accommodating a rigid ejecting rod. According to another embodiment, the lower arm provided in step 203 includes a lower arm recess located substantially centrally within the lower arm, and substantially parallel to the longitudinal axis of the lower arm, for accommodating a pivotally mounted ejecting lever. The upper arm provided in step 203 may further include a lower arm engagement unit which is complementary to the upper arm engagement unit of the upper arm provided in step 201.

Step 205 involves providing an ejecting unit, which according to various embodiments of the invention may take the form of a flexible ejecting rod, a rigid ejecting rod, or an ejecting lever. According to a currently preferred embodiment, step 205 involves providing an ejecting unit in the form of a flexible ejecting rod. According to another embodiment, step 205 involves providing a rigid ejecting rod having a shape substantially like a golf club, the rigid ejecting rod including a rigid shaft, and a head portion located at the distal end of the shaft. According to yet another embodiment, step 205 involves providing an ejecting lever having a shape substantially like a hockey stick, the ejecting lever including a shaft, and a boot portion located at the distal end of the shaft, and the ejecting lever further including a pivot post.

Step 207 involves coupling the lower arm and the upper arm to each other, such that the upper arm is held in slidable engagement with the lower arm and the upper arm is capable of moving reciprocally with respect to the lower arm. Step 207 may involve coupling the lower arm and the upper arm to each other by way of complementary lower arm and upper arm engagement units.

Step 209 involves coupling an actuator to the lower arm such that the actuator pivots with respect to the lower arm at the point of coupling. The actuator may be coupled to the lower arm via a pivot pin to provide a pivot point thereat.

Step 211 involves coupling the actuator to the upper arm of the instrument for providing reciprocal motion of the upper arm relative to the lower arm when the actuator actuates the upper arm. The actuator may be coupled to the upper arm via an upper arm coupling pin.

Step 213 involves mounting the ejecting unit within the lower arm recess such that the ejecting unit is movable within the lower arm recess. According to a currently preferred embodiment, step 213 involves movably mounting the ejecting unit within the lower arm recess such that the ejecting unit is movable from a position where the ejecting unit is completely recessed within the lower arm recess, to a position where a component of the ejecting unit is at least flush with the cutting surface of the lower arm. According to one embodiment of the invention step 213 involves mounting a distal portion of the flexible ejecting rod within the lower arm recess, and mounting a proximal portion of the flexible ejecting rod within a tubular housing. The tubular housing may be secured beneath the lower arm of the instrument or adjacent to the lower arm exterior edge. According to another embodiment of the invention step 213 involves mounting a rigid ejecting rod within the lower arm recess, with a proximal portion of the rigid ejecting rod extending proximally, adjacent and substantially parallel to the lower arm exterior edge. According to another embodiment of the invention step 213 involves mounting the ejecting unit via a pivot post within the lower arm recess, such that the ejecting lever is capable of pivoting within the confines of an upper arm recess and the lower arm recess when the instrument is fully assembled.

According to certain embodiments of the invention, in a further step (step 215, not shown) a flexible ejecting rod, movably mounted within a lower arm recess at its distal end, may be coupled to the actuator at its proximal end such that the flexible ejecting rod moves substantially counter to the upper arm as the upper arm moves in a proximal direction. For example, step 215 may involve coupling the proximal end of the flexible ejecting rod to the actuator, via a securing pin, at a location on the actuator inferior to the pivot point (pivot pin location). Alternatively, according to another embodiment, a rigid ejecting rod movably mounted within a lower arm recess at its distal end may be coupled to the actuator at its proximal end, such that the rigid ejecting rod moves in tandem with the upper arm as the upper arm moves in a proximal direction. For example, step 215 may involve coupling the proximal end of the rigid ejecting rod to the actuator, via a securing pin, at a location on the actuator superior to the pivot point (pivot pin location).

Furthermore, according to a method for making a bone biting instrument, a holding unit may be coupled to the lower arm, or, alternatively the lower arm provided in step 203 may include an integral holding unit, such as a handle. An actuator return unit, which may include various types of springs, may be coupled to the actuator and to the holding unit.

The foregoing embodiments are merely exemplary and are not to be construed as limiting the present invention. The present teaching can be readily applied to other types of apparatuses. The description of the present invention is intended to be illustrative, and not to limit the scope of the claims. Many alternatives, modifications, and variations will be apparent to those skilled in the art.

That is claimed is:

1. An instrument comprising:
    a first arm;
    a second arm, said second arm and said first arm reciprocally engageable for grasping a piece of material between said second arm and said first arm;
    an ejecting unit for ejecting the piece of material; and
    an actuating mechanism arranged such that it both actuates one arm with respect to the other arm and operates said ejecting unit.

2. The instrument of claim 1, wherein said ejecting unit comprises a flexible ejecting rod.

3. The instrument of claim 1, wherein said ejecting unit comprises a rigid ejecting rod.

4. The instrument of claim 1, wherein said actuator actuates said second arm, said second arm reciprocating in slidable engagement with respect to said first arm when said second arm is actuated by said actuator.

5. The instrument of claim 4, wherein said ejecting unit is coupled to said actuator.

6. The instrument of claim 4, wherein said ejecting unit comprises a flexible ejecting rod, said flexible ejecting rod moving counter to said second arm when said second arm is actuated by said actuator.

7. The instrument of claim 4, wherein said actuator is coupled to said first arm by a pivot pin, said ejecting unit comprises a flexible ejecting rod, and said flexible ejecting rod is coupled to said actuator at a location below to said pivot pin.

8. The instrument of claim 6, wherein said instrument further includes a tubular housing for housing a portion of said flexible ejecting rod.

9. The instrument of claim 8, wherein said tubular housing lies external to said first arm.

10. The instrument of claim 4, wherein said ejecting unit comprises a rigid ejecting rod, said rigid ejecting rod moving in tandem with said second arm when said second arm is actuated by said actuator.

11. The instrument of claim 4, wherein said actuator is coupled to said lower arm by a pivot pin, said ejecting unit comprises a rigid ejecting rod, and said rigid ejecting rod is coupled to said actuator at a location above to said pivot pin.

12. An instrument comprising:

a first arm;

a second arm, said second arm and said first arm reciprocally engageable for grasping a piece of material between said second arm and said first arm; and an ejecting unit movable with respect to said first arm, wherein said first arm includes a first arm recess and said ejecting unit is mounted within said first arm recess.

13. The instrument of claim 12, further comprising an actuator pivotally mounted to said first arm.

14. The instrument of claim 13, wherein the actuator is arranged so as to enable a user to both cut and operate the ejecting unit by manipulating the actuator.

15. An instrument comprising:

a first arm;

a second arm, said second arm and said first arm reciprocally engageable for grasping a piece of material between said second arm and said first arm; and an ejecting unit movable with respect to said first arm, wherein said ejecting unit comprises an ejecting lever pivotally mounted within said first arm.

16. The instrument of claim 15, further comprising an actuator pivotally mounted to said first arm.

17. The instrument of claim 16, wherein the actuator is arranged so as to enable a user to both cut and operate the ejecting unit by manipulating the actuator.

18. An instrument comprising:

a first arm;

a second arm, said second arm and said first arm reciprocally engageable for grasping a piece of material between said second arm and said first arm; and an ejecting unit movable with respect to said first arm, wherein said first arm includes a first arm recess and a cutting surface, and said ejecting unit comprises an ejecting lever, said ejecting lever including a pivot post, said ejecting lever is pivotally mounted within said first arm recess via said pivot post, and said ejecting lever is capable of pivoting between an open position and a closed position with respect to said cutting surface.

19. An instrument comprising:

a first arm;

a second arm, said second arm and said first arm reciprocally engageable for grasping a piece of material between said second arm and said first arm; and an ejecting unit movable with respect to said first arm, wherein said second arm includes an elbow, and said ejecting unit comprises a pivot post, and wherein said ejecting unit is forced from an open position to a closed position by said elbow as said elbow reciprocates to a point proximal to pivot post.

20. The instrument of claim 19, further comprising an actuator pivotally mounted to said first arm.

21. The instrument of claim 20, wherein the actuator is arranged so as to enable a user to both cut and operate the ejecting unit by manipulating the actuator.

22. A self-clearing rongeur, comprising:

a lower arm including a lower arm recess and a holding unit;

an actuator pivotally coupled to said lower arm;

an upper arm, said upper arm actuated by said actuator, said upper arm reciprocating in slidable engagement with respect to said lower arm when said upper arm is actuated by said actuator; and an ejecting unit movably mounted with respect to said lower arm.

23. The self-clearing rongeur as claimed in claim 22, wherein said ejecting unit is selected from the group consisting of a flexible ejecting rod, a rigid ejecting rod, and an ejecting lever.

24. The self-clearing rongeur as claimed in claim 22, wherein said ejecting unit comprises a flexible ejecting rod, said flexible ejecting rod coupled to said actuator.

25. The self-clearing rongeur as claimed in claim 24, wherein said actuator is pivotally coupled to said lower arm via a pivot pin, and said flexible ejecting rod is coupled to said actuator at a location below to said pivot pin.

26. The self-clearing rongeur as claimed in claim 22, wherein said ejecting unit comprises a rigid ejecting rod, and said rigid ejecting rod is coupled to said actuator.

27. The self-clearing rongeur as claimed in claim 26, wherein said actuator is pivotally coupled to said lower arm via a pivot pin, and said rigid ejecting rod is coupled to said actuator at a location above to said pivot pin.

28. A self-clearing rongeur, comprising:

a first arm including a first arm recess and a holding unit;

an actuator pivotally coupled to said first arm;

a second arm, said second arm actuated by said actuator, and reciprocating in slidable engagement with respect to said first arm when said second arm is actuated by said actuator; and an ejecting unit movably mounted with respect to said first arm, wherein said ejecting unit comprises an ejecting lever, said ejecting lever being pivotally mounted within said first arm recess via a pivot post.

29. The self-clearing rongeur as claimed in claim 28, wherein said first arm further includes a foot plate and a cutting surface, and wherein said ejecting lever is capable of pivoting between an open position and a closed position with respect to said cutting surface.

30. A self-clearing rongeur, comprising:

a first arm including a first arm recess and a holding unit;

an actuator pivotally coupled to said first arm;

a second arm, said second arm actuated by said actuator, and reciprocating in slidable engagement with respect to said first arm when said second arm is actuated by said actuator, wherein said second arm includes an elbow and a second arm recess, said second arm recess having a second arm recess superior portion and a second arm recess inferior portion, said elbow being located between said second arm recess superior portion and said second arm recess inferior portion; and an ejecting unit movably mounted with respect to said first arm.

31. The self-clearing rongeur as claimed in claim 30, wherein said second arm further includes a second arm interior edge and said elbow is aligned with said second arm interior edge.

32. The self-clearing rongeur as claimed in claim 30, wherein said ejecting lever is forced from the open position to the closed position by said elbow as said elbow reciprocates to a point proximal to said pivot post.

33. A self-clearing rongeur, comprising:
   a stationary lower arm including a holding unit, a lower arm distal end, a lower arm engagement unit, and a lower arm recess;
   an actuator pivotally coupled to said stationary lower arm;
   an actuator return unit coupled to said actuator and to said holding unit;
   a movable upper arm including an upper arm engagement unit, said upper arm engagement unit cooperating with said lower arm engagement unit to hold said upper arm in slidable engagement with said lower arm, said upper arm actuated by said actuator, said upper arm reciprocating in slidable engagement with respect to said lower arm when said upper arm is actuated by said actuator; and
   an ejecting unit located within said lower arm recess.

34. The self-clearing rongeur as claimed in claim 33, wherein said ejecting unit is selected from the group consisting of a flexible ejecting rod, a rigid ejecting rod, and an ejecting lever.

35. The self-clearing rongeur as claimed in claim 33, wherein said ejecting unit comprises a flexible ejecting rod, said flexible ejecting rod coupled to said actuator, said flexible ejecting rod moving substantially counter to said upper arm when said upper arm is actuated by said actuator.

36. A method for making a bone biting instrument, comprising the steps of:
   a) providing an upper arm of the instrument;
   b) providing a lower arm of the instrument, the lower arm including a lower arm recess;
   c) providing an ejecting unit;
   d) coupling the upper arm and the lower arm to each other;
   e) coupling the lower arm to an actuator;
   f) coupling the upper arm to the actuator; and
   g) mounting the ejecting unit within the lower arm recess.

37. The method for making a bone biting instrument as claimed in claim 36, further comprising the step of h) coupling the ejecting unit to the actuator.

38. The method for making a bone biting instrument as claimed in claim 37, wherein said step c) comprises providing an ejecting unit including a flexible ejecting rod, said step e) comprises coupling the lower arm to the actuator via a pivot pin, and said step h) comprises coupling the flexible ejecting rod to the actuator at a location on the actuator below to the pivot pin.

39. The method for making a bone biting instrument as claimed in claim 37, wherein said step c) comprises providing an ejecting unit including a rigid ejecting rod having a shaft and a head portion, said step e) comprises coupling the lower arm to the actuator via a pivot pin, and said step h) comprises coupling the rigid ejecting rod to the actuator at a location on the actuator above to the pivot pin.

40. The method for making a bone biting instrument as claimed in claim 36, wherein said step c) comprises providing an ejecting unit including an ejecting lever having a pivot post, a shaft, and a boot.

41. The method for making a bone biting instrument as claimed in claim 40, wherein said step g) comprises pivotally mounting the ejecting lever, via the pivot post, within the lower arm recess.

42. The method for making a bone biting instrument as claimed in claim 36, wherein said step a) comprises providing an upper arm including an elbow and an upper arm recess, wherein the upper arm recess comprises an upper arm recess superior portion and an upper arm recess inferior portion, and wherein the elbow is located between the upper arm recess superior portion and the upper arm recess inferior portion.

43. The method for making a bone biting instrument as claimed in claim 36, wherein said step b) comprises providing a lower arm further including a foot plate, and the lower arm recess extending into the foot plate.

44. The method for making a bone biting instrument as claimed in claim 40, wherein said step g) comprises pivotally mounting the ejecting lever, via the pivot post, within the lower arm recess such that, when the instrument is fully assembled, the ejecting lever is capable of pivoting within the confines of the upper arm recess and the lower arm recess.

45. The method for making a bone biting instrument as claimed in claim 36, wherein said step d) comprises coupling the lower arm and the upper arm to each other such that the upper arm is held in slidable engagement with the lower arm and the upper arm is capable of moving reciprocally against the lower arm.

46. The method for making a bone biting instrument as claimed in claim 36, further comprising the step of coupling an actuator return unit to the actuator.

47. An instrument comprising:
   a non-cutting arm, said non-cutting arm including a cutting surface;
   a cutting arm, said cutting arm and said non-cutting arm reciprocally engageable for grasping a piece of material between said cutting arm and said non-cutting arm;
   an ejecting unit for ejecting the piece of material; and
   an actuating mechanism arranged such that it both actuates one arm with respect to the other arm and operates the ejecting unit.

48. The instrument of claim 47, wherein said non-cutting arm includes a noncutting arm recess and said ejecting unit is mounted within said non-cutting arm recess.

49. The instrument of claim 47, wherein said ejecting unit comprises a rigid ejecting rod.

50. The instrument of claim 47, wherein said ejecting unit comprises a flexible ejecting rod.

51. The instrument of claim 47, wherein said ejecting unit comprises an ejecting lever pivotally mounted by a pivot post within said non-cutting arm.

52. The instrument of claim 51, wherein said cutting arm includes an elbow, and wherein said ejecting unit is forced from an open position to a closed position by said elbow as said elbow reciprocates to a point proximal to the pivot post.

53. The instrument of claim 47, wherein said actuator actuates said cutting arm, said cutting arm reciprocating in slidable engagement with respect to said non-cutting arm when said cutting arm is actuated by said actuator.

54. The instrument of claim 53, wherein said actuator is coupled to said non-cutting arm by a pivot pin, and said ejecting unit is coupled to said actuator.

55. The instrument of claim 53, wherein said ejecting unit comprises an ejecting rod, said ejecting rod moving counter to said cutting arm when said cutting arm is actuated by said actuator.

56. The instrument of claim 55, wherein said instrument further comprises a tubular housing for housing a portion of said ejecting rod.

\* \* \* \* \*